(12) United States Patent
Collins et al.

(10) Patent No.: US 7,943,367 B2
(45) Date of Patent: May 17, 2011

(54) HIGH-THROUGHPUT ELECTROPORATION CHAMBER WITH FUNCTIONAL LID FOR RISK REDUCTION

(75) Inventors: Michelle Collins, Oakland, CA (US); Steven Kulisch, Pleasant Hill, CA (US); Charles W. Ragsdale, Concord, CA (US); Teresa Rubio, El Cerrito, CA (US); Gary Bouchard, Santa Cruz, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 909 days.

(21) Appl. No.: 11/857,525

(22) Filed: Sep. 19, 2007

(65) Prior Publication Data

US 2008/0156640 A1 Jul. 3, 2008

Related U.S. Application Data (60) Provisional application No. 60/826,353, filed on Sep. 20, 2006.

(51) Int. Cl.
*C12M 1/42* (2006.01)
*C12M 3/00* (2006.01)

(52) U.S. Cl. .................................................. 435/285.2
(58) Field of Classification Search .............. 435/285.2
See application file for complete search history.

(56) References Cited

U.S. PATENT DOCUMENTS

| 4,682,891 | A  | * | 7/1987  | de Macario et al. ......... 356/244 |
| 6,078,490 | A  | * | 6/2000  | Walters ........................ 361/88 |
| 6,653,124 | B1 | * | 11/2003 | Freeman .................... 435/297.1 |
| 6,686,193 | B2 | * | 2/2004  | Maher et al. ............. 435/285.2 |
| 6,878,538 | B1 | * | 4/2005  | Walters et al. ........... 435/285.2 |
| 2003/0129716 | A1 | * | 7/2003 | Ragsdale et al. ........... 435/173.6 |
| 2006/0121610 | A1 | * | 6/2006 | Rubinsky et al. ............ 435/446 |

FOREIGN PATENT DOCUMENTS

WO WO 2004/050866 * 6/2004

* cited by examiner

*Primary Examiner* — Walter D Griffin
*Assistant Examiner* — Lydia Edwards
(74) *Attorney, Agent, or Firm* — Kilpatrick Townsend and Stockton LLP.; M. Henry Heines (57) ABSTRACT

A chamber that includes electrical contacts and a protective lid with a manually operated release is designed to receive a multi-well electroporation plate and to allow high-throughput electroporation on the well contents with minimal risk of electrical shock to the user and minimal opportunity for sample loss and contamination.

9 Claims, 7 Drawing Sheets

HIGH-THROUGHPUT ELECTROPORATION CHAMBER WITH FUNCTIONAL LID FOR RISK REDUCTION

CROSS-REFERENCE TO RELATED APPLICATION

This application claims the benefit of U.S. Provisional Patent Application No. 60/826,353, filed Sep. 20, 2006, the contents of which are incorporated herein by reference in their entirety.

BACKGROUND OF THE INVENTION

1. Field of the Invention

This invention resides in the field of electroporation and electroporation chambers.

2. Description of the Prior Art

Electroporation, or electric pulse-driven transfection, is widely used for impregnating membranous structures, such as living biological cells, liposomes, and vesicles, with exogenous molecules. The liquid in which the structures is suspended is typically an aqueous solution of the exogenous species in a high-conductivity buffer. Normal saline is commonly used as the buffer since, in addition to offering relatively low resistance to an electric current, normal saline provides an environment that is favorable to the viability of most membranous structures. The transfection of multiple samples of membranous structure suspensions either simultaneously or in rapid succession by electroporation is known as "high-throughput electroporation," a procedure that is useful in siRNA experiments, in research using cDNA libraries, and in numerous other manipulations of membranous structures that are practiced in biotechnology laboratories. In high-throughput electroporation, the samples undergo transfection in the wells of a multi-well plate that contains electrodes embedded in each well. One example of such an electroporation plate is sold by BTX Instrument Division, Harvard Apparatus, Inc. (Holliston, Mass., USA), and described in an International Patent Application Publication No. WO 2004/050866 A1, entitled "Large-Scale Electroporation Plates, Systems, and Methods of Use" (Genetronics, Inc., applicant; Gamelin, A., et al., inventors), published under the Patent Cooperation Treaty on Jun. 17, 2004. While various aspects of high-throughput electroporation can be automated, operator involvement and intervention are still needed, and hazards to the operator arise from the presence of an electric field and the possible exposure to live electric contacts. The handling of the liquid media in which the cells are suspended also entails a risk of sample loss, cross-sample contamination, or both.

These and other limitations and sources of operational inefficiency and risk to the operator are addressed by the present invention.

SUMMARY OF THE INVENTION

The present invention resides in a high-throughput electroporation chamber that offers enhanced protection to the user against electrical shocks, as well as improved ease in handling multiple samples of liquid with a reduced risk of spillage or contamination. The chamber is designed for use with high-throughput electroporation plates such as those described above, and preferably those with electrodes that are exposed beyond the perimeters of the wells for contact for contact with a source of electrical power. The chamber contains a releasable lid that protects the user from inadvertent contact with the energized electrical components in the chamber by disengaging those components from the electrical power supply when the lid is raised. When a high-throughput plate is secured in the chamber in a manner that establishes reliable electrical contact between the plate and electric leads in the chamber interior, release of the lid eases the plate from these leads in a non-jarring manner that avoids undesirable jostling of the liquids in the plate wells. Both the interruption of electrical contact and the release of the high-throughput plate from its secure retainment in the chamber are achieved by a single release mechanism that operates in conjunction with the opening of the lid, thereby assuring that neither the inadvertent opening of the lid nor the operation of the chamber by an inexperienced technician will result in exposure of the technician to electrical hazards or cause loss or contamination of the samples in the plate.

These and other features, objects, advantages, and embodiments of the invention will be readily apparent and understood from the description that follows.

DETAILED DESCRIPTION OF THE INVENTION AND PREFERRED EMBODIMENTS

Electroporation chambers of the present invention are useful for the performance of electroporation in high-throughput electroporation plates in general. Preferred plates are those with electrodes that protrude either downward from the bottoms of the plates or laterally from the sides of the plates for seizure by electrical contacts within the chamber. One example of such a plate is the BTX plate described in WO 2004/050866 A1 above; other examples are those described in co-pending U.S. patent application Ser. No. 11/627,235, filed Jan. 25, 2007, entitled "Apparatus for High-Throughput Electroporation" (inventors Ragsdale, C. W., et al.) and co-pending U.S. patent application Ser. No. 11/683,893, filed Mar. 8, 2007, entitled "Composite Electroporation Plate With Interchangeable Well Inserts" (inventors Ragsdale, C. W., et al.).

Principal components of the electroporation chamber of this invention are a well that is sized to receive a high-throughput electroporation plate and that contains electrical contacts or leads to supply power to the plate, and the aforementioned lid that provides both mechanical and electrical disengagement functions when opened. The electric power connections within the well are most conveniently provided by a printed circuit board, particularly one whose circuitry can select individual wells or groups of wells on the plate, can distribute the power in an effective manner among the different portions of the plate, and can implement pulsing protocols that can be directed by a controller. The printed circuit board preferably contains electrical contacts that will grasp the exposed electrodes of the electroporation plate to form both a secure electrical connection and a secure mechanical connection. A further feature of preferred embodiments is the inclusion of guide elements formed in one or more of the interior surfaces of the well, the guide elements serving to direct both the insertion of the plate and its orientation such that the electrodes of the plate are in proper alignment with the electrical contacts in the well. These guides or further guides can also support the plate in an orientation parallel to the printed circuit board. Power can be supplied to the chamber by conventional means such as an electrical cable. In certain embodiments, the well is shaped to allow the placement of a cover over the high-throughput plate when the lid is open.

The lid can be attached to the well by any conventional mechanical connection that will allow easy removal or opening of the lid by manual operation. Preferably, the connection is a hinge connection, and most preferably a spring-loaded hinge connection that will urge the lid toward an open position when the lid is released. A latch can be included to secure the lid in a closed position, particularly a latch that is readily releasable by a finger-operated release.

Certain chambers within the scope of this invention further include electrical interlocks attached to, or otherwise associated with, the lid that interrupt the power supply to the plate when the lid is open. An additional interlock that is associated with the plate itself in some embodiments is a metal strip that is molded into the plate to contact the circuitry on the printed circuit board in such a manner that high voltage in the board is interrupted when the plate is removed from the well. A further interlock can be included in the instrumentation attached to the chamber. This last interlock, which can be made available through extra contacts and a jumper in the chamber cable, is one that interrupts high voltage when irregularities arise in the external power supply, or when the cable of the chamber is unplugged, or both.

While the features defining this invention are capable of implementation in a variety of constructions, the invention as a whole will be best understood by a detailed examination of a specific embodiment. One such embodiment is shown in the drawings.

Figure 1:
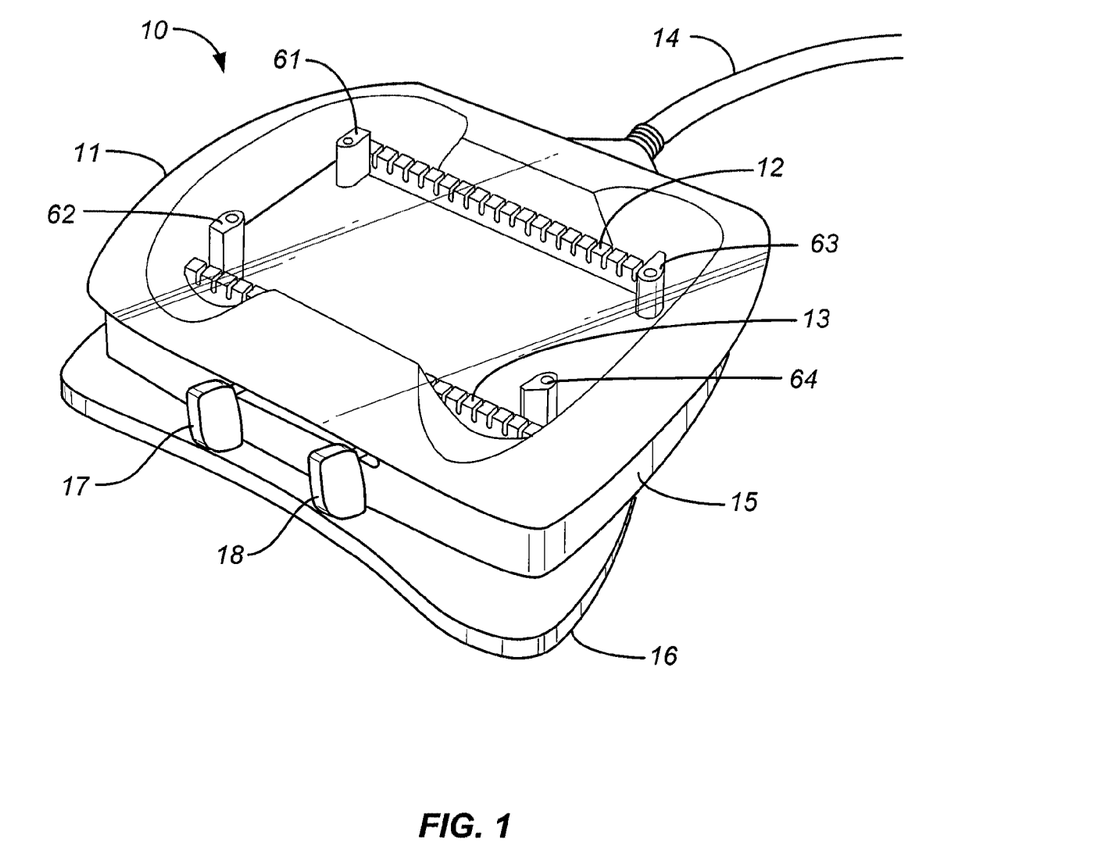
FIG. 1 is a perspective view of an electroporation chamber in accordance with the present invention.

FIG. 1 is an external view of a chamber 10 in accordance with the present invention with a lid 11 in a closed position. The lid 11 in this example is transparent to allow the user to observe the samples during the procedure, and in the case of FIG. 1 to render the interior of the chamber visible. The chamber 10 in this Figure is empty, representing its condition prior to the insertion of the multi-well plate containing samples to be transfected by electroporation. Connection features in the interior of the chamber are contained within two raised and slotted hollow ridges 12, 13 that run parallel to each other along the lengthwise sides of the well interior. Both the ridges and the connection features are described below.

Electric power is supplied to the electrical components in the chamber by a power cable 14 emerging from the rear of the chamber, the cable leading to a high-throughput box (not shown). The high-throughput box contains instrument electronics that control such features as the level of the power supplied to the chamber, the waveform of the power, the sequence of electric leads that will be energized, and the timing of the sequence. The high-throughput box can also contain instrument electronics to monitor the voltage that is supplied to each well of the plate and the current that results from the voltage to ensure that all wells receive electrical power in accordance with the operation desired by the user.

The exterior of the closed chamber is defined by the lid 11, the lateral walls that define the well 15 of the chamber, and a supporting foot or base 16 of the chamber. Protruding through the one of the lateral walls of the well 15 are a pair of finger tabs 17, 18 that are used for releasing the lid 11 from the well and for the functions associated with the release of the lid, namely the disengagement of the electrodes on the well plate from the electrical contacts on the circuit board and the mechanical release of the plate from the well. The operations of these tabs and their associated mechanisms are explained below.

Figure 2:
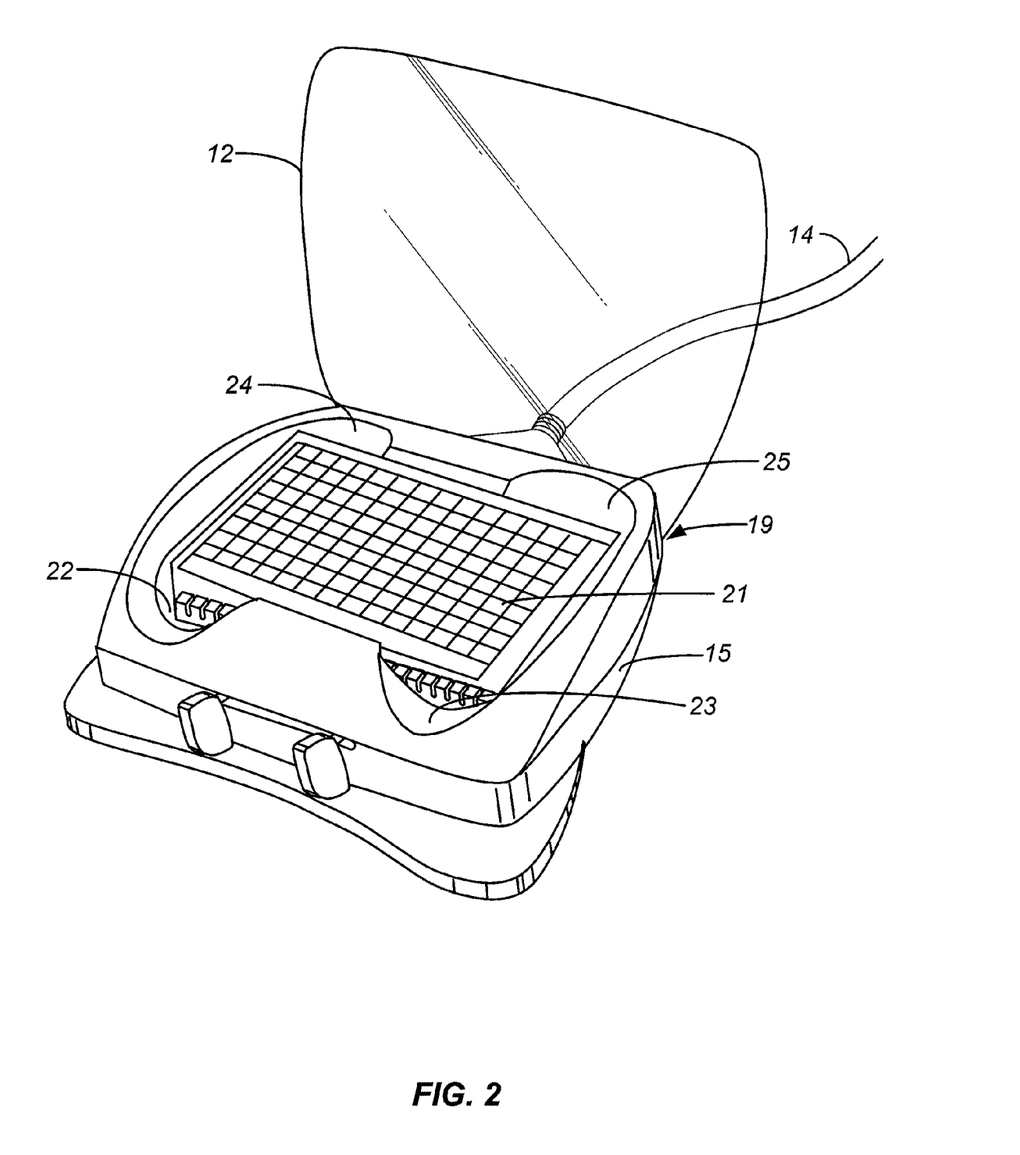
FIG. 2 is a perspective view of the electroporation chamber of FIG. 1 with the lid raised.

FIG. 2 shows the same chamber 10 with the lid 11 open and a high-throughput electroporation plate 21 inserted. The high-throughput electroporation plate is also referred to herein as a "sample plate." The lid 11 is joined to the well 15 by a hinge-type connection at the rear longitudinal side 19 of the well 15. With the lid raised, the contoured upper rim of the well 15 is made visible. The rim contains depressions 22, 23, 24, 25 to permit the user to grasp the sides of the sample plate 21 by the user's fingers when lifting the sample plate out of the chamber.

Figure 3:
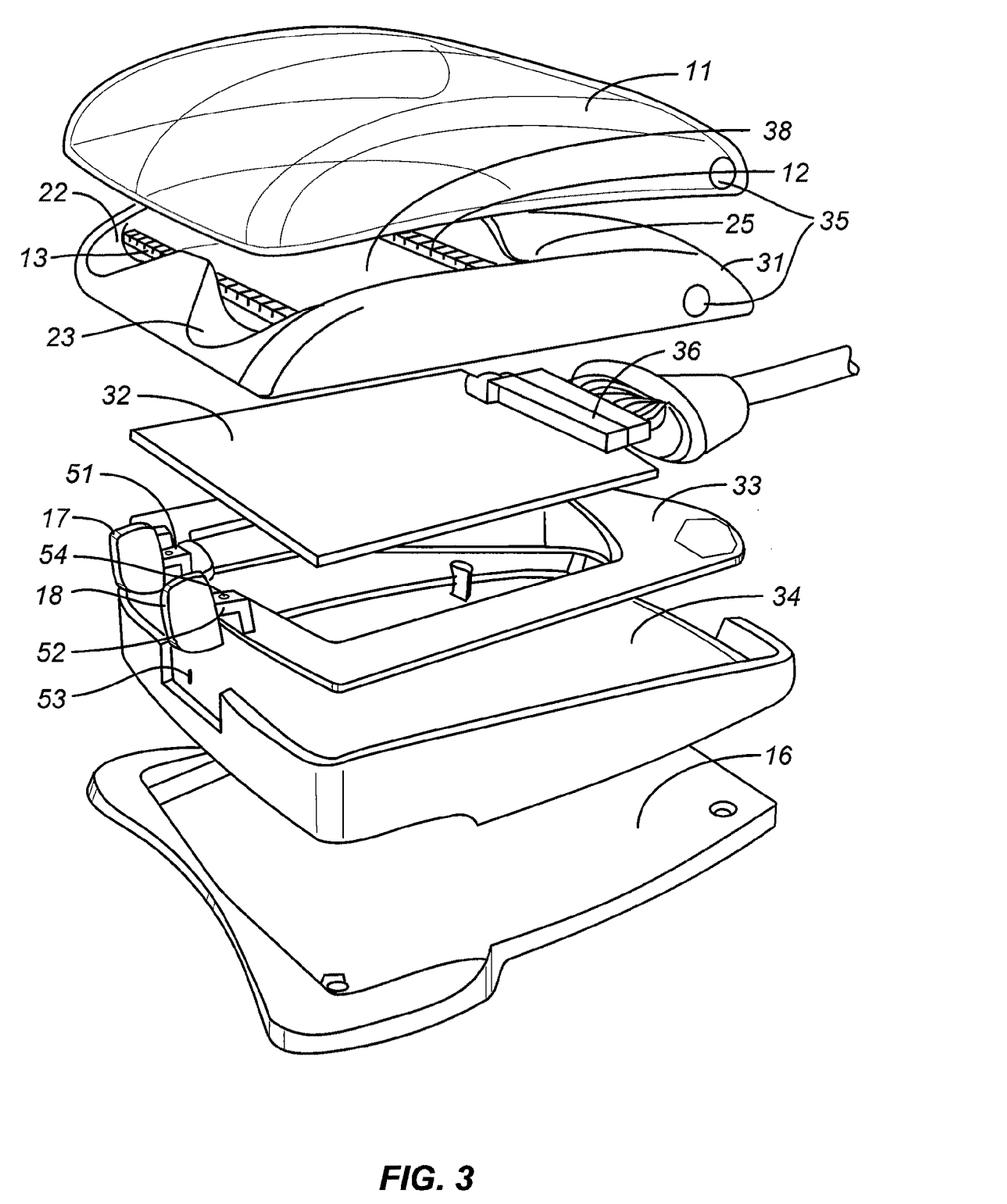
FIG. 3 is an exploded view of the components of the electroporation chamber of FIGS. 1 and 2.

FIG. 3 is an exploded perspective view of the chamber without the sample plate. From the top down, the components shown are the lid 11, an upper plate 31, a printed circuit board 32, a finger tab frame 33, a lower plate 34, and the foot 16 that serves as the support base of the chamber. The upper plate 31 and the lower plate 34 together form the well 15 of the preceding Figures. The upper plate 31 and the lower plate 34 are either bonded together or joined by other conventional means of connection such as rivets or screws, and the lid 11 and upper plate 31 are joined by the hinge connection 35 mentioned above. Attached to the rear edge of the printed circuit board 32 is a cable connector 36, and extending upward from the upper surface of the printed circuit board 32, although not shown in FIG. 3, are upwardly extending leads arranged in two parallel rows, one near the front edge of the printed circuit board and other near the rear edge. Convenient types of leads for this structure are those known in the art as "tulip" or "double-beam" contacts, which are paired contacts that resiliently grasp an electric conductor to establish both electrical contact and a stable mechanical connection. The tulip contacts extend upward into the hollow interiors of the slotted hollow ridges 12, 13, which are molded into the upper plate 31. The slotted hollow ridges protect the user from inadvertent manual contact with the tulip contacts, while protecting the tulip contacts from damage, and yet allow full access of the sample plate electrodes to the tulip contacts through the slots. The tulip contacts and the hollow ridges are both shown in FIGS. 4a and 4b and described in detail below.

Figure 4A:
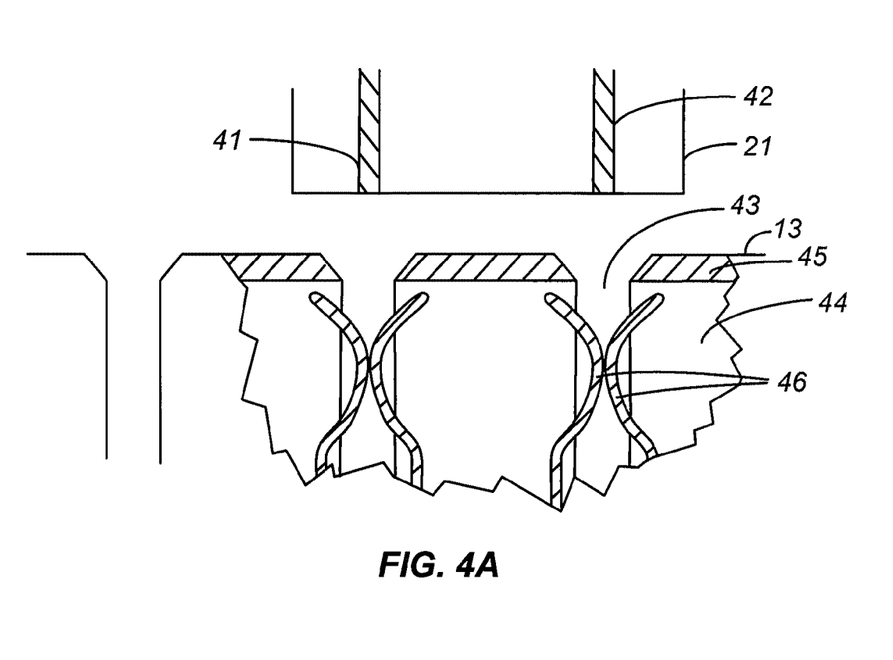
FIGS. 4*a* and 4*b* are partial views of the components serving as electrical contacts between a high-throughput electroporation plate and the electroporation chamber of FIGS. 1 and 2, with sections removed to show the interior.
Figure 4B:
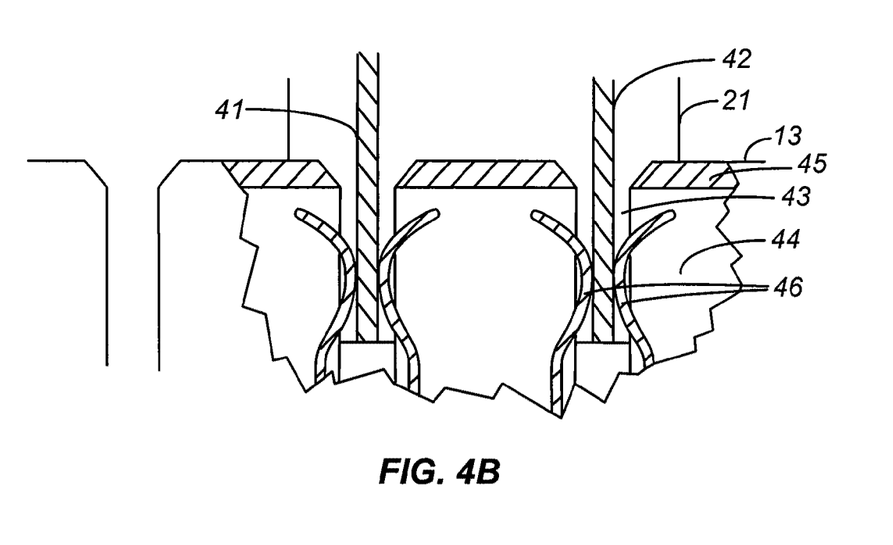

The sample plate (not shown in FIG. 3) containing the samples on which electroporation is to be performed rests in the central depression 38 of the upper plate 31 of the well. The electrodes that extend from the sample plate are typically extensions of sample plate electrodes that run parallel to the shorter sides of the sample plate. FIGS. 4a and 4b show the bottom of the sample plate 21 including the end of one row of wells with the exposed protruding ends of two plate electrodes 41, 42, one along each side of the well row. Also shown is one of the two hollow ridges 13. The ridge is interrupted by slots 43 and its hollow interior 44 is covered at the top 45 but open at the sides to the slots 43. The tulip contacts 46 arising from the printed circuit board 32 (FIG. 3) extend into the hollow interior 44 of the ridge and protrude into the slots 43 where they grasp the protruding electrodes 41, 42 when the electrodes are lowered into the slots. FIG. 4a shows the electrodes 41, 42 being lowered into the slots 43, while FIG. 4b shows the electrodes fully lowered and in electrical contact with the tulip contacts 46. The user thus establishes electrical contact between the sample plate 21 and the printed circuit board 32 by simply pressing the plate down into the central depression 38 of the upper plate 31.

Returning to FIG. 3, the finger tab frame 33 fits inside the lateral walls of the lower plate 34. The finger tabs 17, 18 are joined to the frame 33 by necks 51, 52 that pass through a notch 53 in the lower plate, placing the finger tabs 17, 18 outside the walls of the lower plate 34. Embedded in the upper surface of one or both of the necks 51, 52 is a magnet 54 that is aligned with another magnet or metal insert (not visible) embedded in the opposing surface on the front edge of the lid 11 directly opposite the magnet, the magnet and metal insert operating as a latch to hold the lid closed. To release the latch and allow the lid 11 to be raised, the user draws the tabs together by simple finger pressure between the thumb and forefinger. The tabs then return to their open position when the finger pressure is removed.

Squeezing together of the finger tabs 17, 18 achieves two functions. The first is to draw the magnet 54 out of alignment, and hence contact, with the metal insert (or magnet) in the lid 11, thereby disengaging the latch. The hinge 35 joining the rear of the lid 11 to the upper plate 31 is spring-biased to urge the lid upwards once the latch is disengaged, thereby causing the lid to rise slowly and sufficiently to allow the user to manually lift the lid further. The second function of the finger tabs is to lift the sample plate from the upper chamber plate 31 and thereby disengage the plate electrodes 41, 42 protruding from the edges of the sample plate from the tulip contacts 46 on the upper side of the circuit board 32. The mechanism by which this occurs is explained below.

Figure 5:
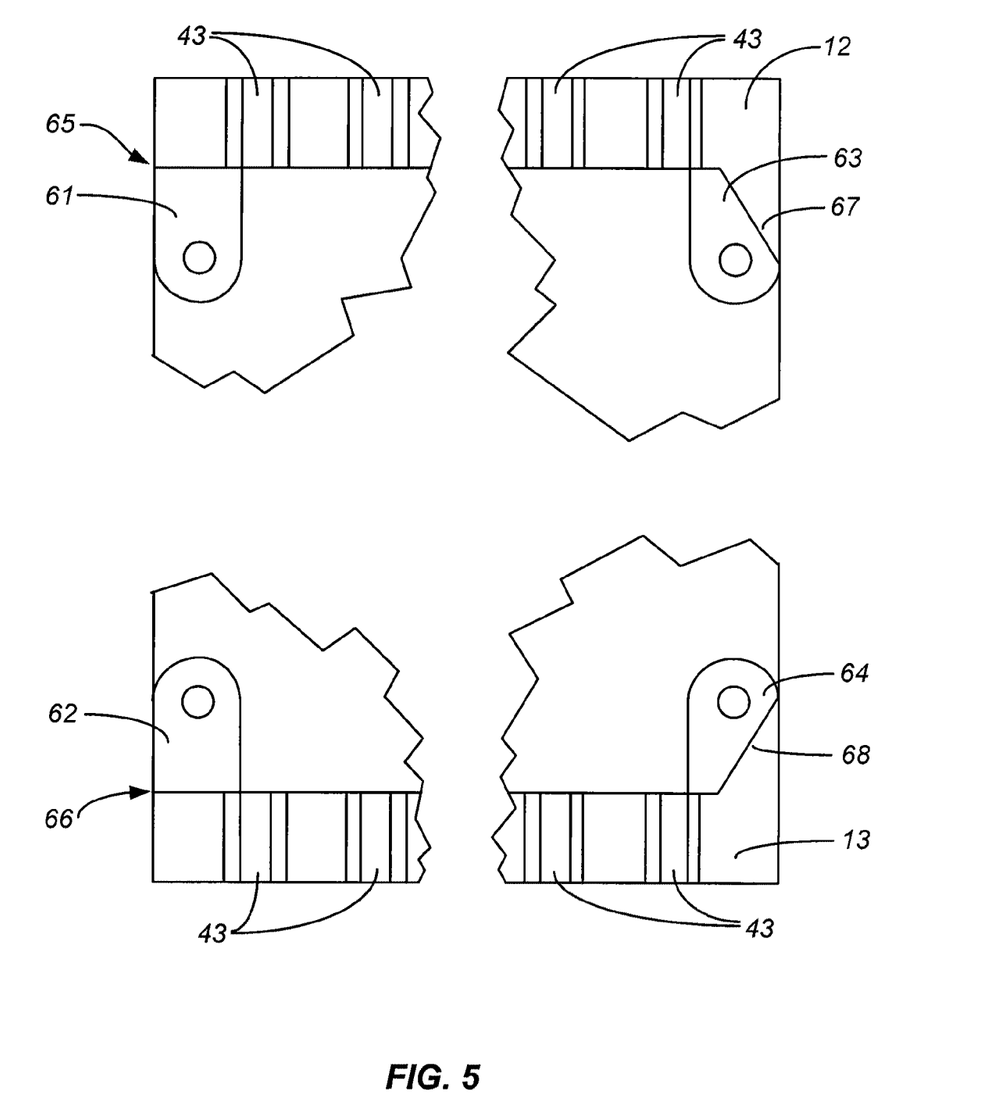
FIG. 5 is a top view of one of the internal components of the electroporation chamber of the FIGS. 1 and 2.

Referring to FIG. 1, the interior of the upper well plate 31 contains four posts 61, 62, 63, 64 at locations corresponding to the four corners of the sample plate. The plate rests on these posts which, by supporting the plate, maintains the plate in a parallel relation with the circuit board and with other components of the chamber. The posts also serve as guides for insertion of the sample plate into the well and doing so in the proper orientation. The posts are shown in a top view in FIG. 5 and are not identical in shape. The differences lie in the outer corners of the posts, the two posts on one side 61, 62 having outer corners 65, 66 forming right angles, and the two posts on the other side 63, 64 having outer corners that are cut at acute angles to form angled walls 67, 68. These differences allow the sample plate to be inserted in only one orientation. Holes or indentations on the underside of the sample plate have shapes complementary to the posts to receive the upper ends of the posts, the right-angle-cornered posts 61, 62 mating with right-angle-cornered holes and the cut-cornered posts 63, 64 mating with cut-cornered holes, thereby preventing the plate from being installed backwards, i.e., when rotated 180°.

Figure 6A:
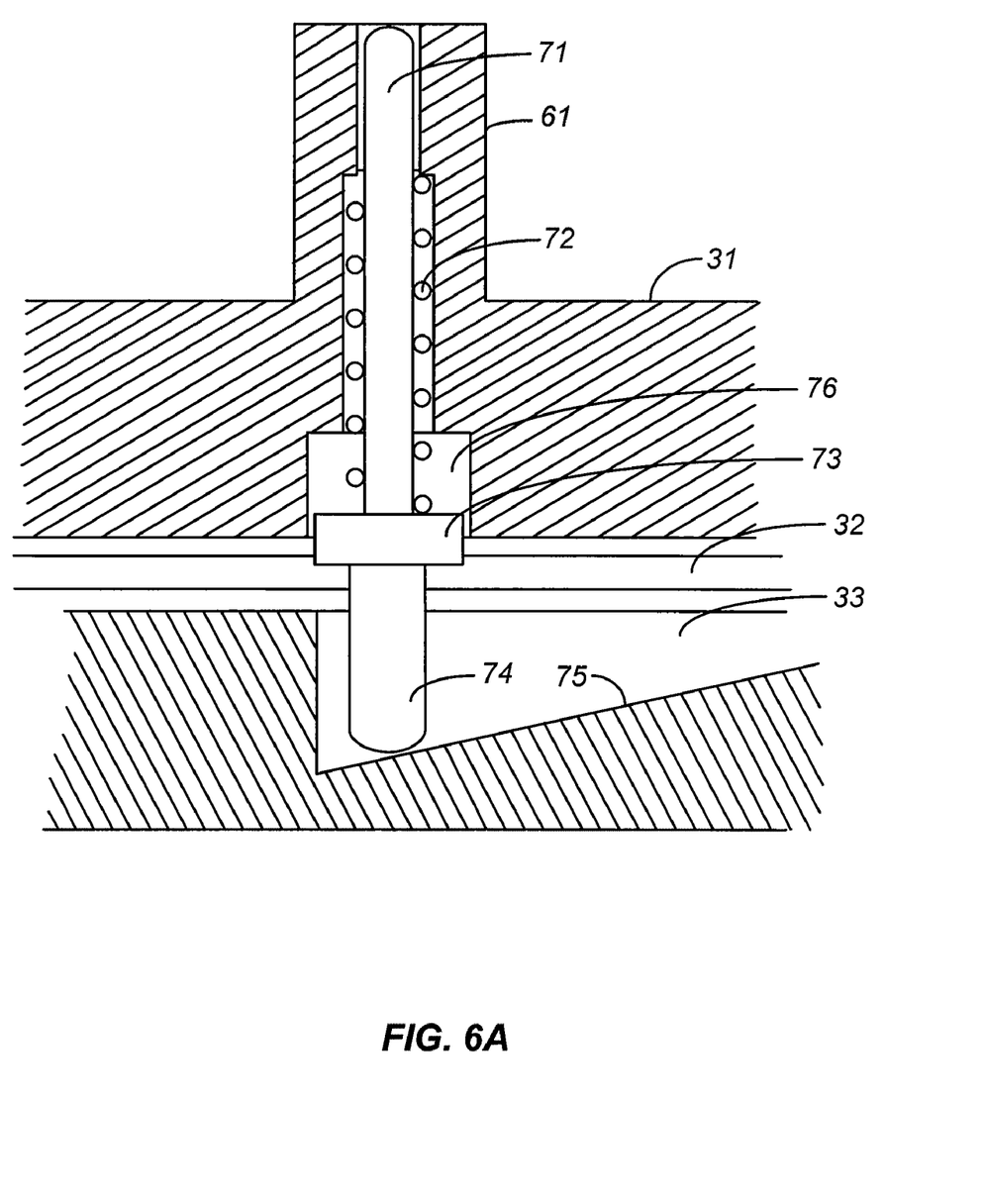
FIGS. 6*a* and 6*b* are front views in partial cross section of the release mechanism for the release of a high-throughput electroporation plate from the electroporation chamber of FIGS. 1 and 2.
Figure 6B:
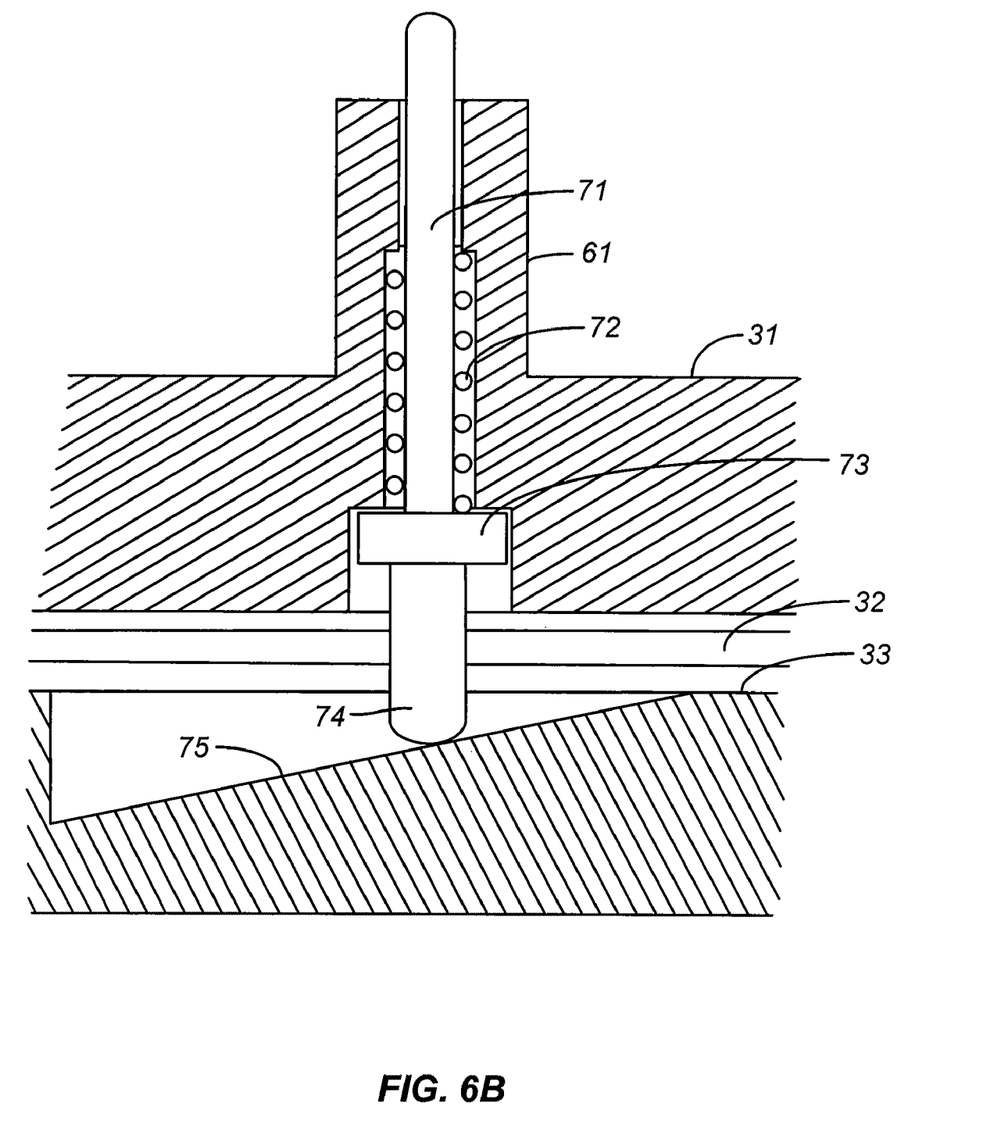

Each post also contains an internal lifter pin that causes the sample plate to be lifted off the posts when the chamber lid 11 is raised. The structure and operation of these lifter pins are shown in the enlarged views of one post 61 in FIGS. 6a and 6b. FIGS. 6a and 6b also show the upper well plate 31, the printed circuit board 32, and the finger tab frame 33. The post 61 is hollow, and the lifter pin 71 extends into the post interior and is encircled by a spring 72 that urges the lifter pin downward. The lifter pin also includes a flange 73 and an extension 74 at the base of the flange 73. A ramp 75 formed in the surface of the finger tab frame 33 contacts the lifter pin extension 74 and pushes the entire lifter pin 71 upward as the ramp 75 moves laterally when the frame is compressed as the user squeezes the finger tabs together. Thus pushed upward, as shown in FIG. 6b, the lifter pin 71 protrudes from the top of the post 61 to push the sample plate above and off of the post and to disengage the electrodes on the sample plate from the tulip contacts on the printed circuit board. As the pin is raised, the flange 73 moves upward within a recess 76 in the plate 31, compressing the spring 72. Release of the finger tabs causes the frame 33 to return to its relaxed position and the ramp 75 to shift back. As the ramp 75 returns to its relaxed position, the spring 72 urges the lifter pin 71 back down. All four posts 61, 62, 63, 64 have lifter pins constructed in the same manner as that shown in FIGS. 6a and 6b, each with springs, each with a corresponding recess in the upper well plate 31, and each with a corresponding ramp in the finger tab frame 33, such that squeezing of the finger tabs causes all four lifter pins to rise simultaneously, and release of the finger tabs causes all four lifter pins to simultaneously return to their retracted positions.

While the foregoing description describes various alternatives, still further alternatives will be apparent to those who are skilled in the art and are within the scope of the invention.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. An electroporation chamber for receiving and supplying power to a multi-well electroporation plate that has exposed electrodes, said electroporation chamber comprising:
    a well having internal features comprising electrical contacts arranged to mate with said electrodes;
    a removable lid configured to cover said well; and
    a finger-operated release constructed to simultaneously raise said lid from said well and lift said electroporation plate to disengage said electrodes from said electrical contacts.

2. The electroporation chamber of claim 1 wherein said lid is attached to said well by a hinge connection and is spring-biased toward a raised position.

3. The electroporation chamber of claim 1 wherein said internal features of said well further comprise a printed circuit board, and wherein said electrical contacts are mounted to said printed circuit board.

4. The electroporation chamber of claim 3 wherein said electrical contacts protrude from the surface of said printed circuit board and said internal features further comprises hollow enclosures to prevent manual contact with said electrical contacts while providing openings for access of said electrodes to said electrical contacts.

5. The electroporation chamber of claim 1 further comprising a latch that releasably secures said lid to said well and is released by action of said finger-operated release.

6. The electroporation chamber of claim 5 wherein said latch is a pair of magnetic contacts.

7. The electroporation chamber of claim 1 wherein said features further comprise guides for insertion and orientation of said electroporation plate.

8. The electroporation chamber of claim 1 wherein said lid is transparent.

9. The electroporation chamber of claim 1 further comprising an electrical power supply cable connected to supply electric power to said electrical contacts, and an electrical interlock arranged to interrupt power said power supply when said lid is raised.

* * * * *